United States Patent [19]

Caston

[11] Patent Number: 5,185,157
[45] Date of Patent: Feb. 9, 1993

[54] TREATMENT OF REFRACTORY EOSINOPHILIA-MYALGIA SYNDROME WITH L-TRYPTOPHAN COMPOSITION

[76] Inventor: John C. Caston, 108 Cinder Ter., Spartanburg, S.C. 29302

[21] Appl. No.: 518,499

[22] Filed: May 2, 1990

[51] Int. Cl.5 .......... A61K 47/42; A61K 9/20; A61K 31/40; C07K 3/04
[52] U.S. Cl. .......... 424/456; 424/439; 424/441; 424/463; 424/464; 424/451; 514/419; 514/923; 530/403; 530/832
[58] Field of Search .......... 424/439, 441, 456, 451, 424/463, 464; 514/419, 923; 530/403, 832

[56] References Cited

U.S. PATENT DOCUMENTS 4,897,380  1/1990  Pollack .......... 514/23

FOREIGN PATENT DOCUMENTS 54-52073  4/1979  Japan .......... 514/419

OTHER PUBLICATIONS

"The Clinical Spectrum of the Eosinophilia-Myalgia Syndrome Associated with L-Tryptophan Ingestion--Clinical Features in 20 Patients and Aspects of Pathophysiology".

*Primary Examiner*—Thurman K. Page
*Assistant Examiner*—Carlos Azpuru
*Attorney, Agent, or Firm*—Arthur R. Eglington

[57] ABSTRACT

A method of treating a human patient with refractory Eosinophilia Myalgia Syndrome via oral administration of an effective dosage range of from 1000 mg. to 3000 mg. of a pharmaceutical composition, in unit dosage form, comprising a minor amount of a solid or liquid carrier and a major amount of the amino acid, pharmaceutical grade L-tryptophan, or its acid addition salt, with both of the carriers and the amino acid to be selected to exclude the zinc, magnesium, and calcium containing salts as adjuvants.

10 Claims, No Drawings

TREATMENT OF REFRACTORY EOSINOPHILIA-MYALGIA SYNDROME WITH L-TRYPTOPHAN COMPOSITION

TECHNICAL FIELD

This invention relates to the treatment of human Eosinophilia-Myalgia syndrome with selected amino acids.

BACKGROUND OF THE INVENTION

Eosinophilias are naturally occurring components in the mammalian blood which have activities like that of other white blood cells (lymphocytes). Eosinophilia means "an increase of such eosinophils circulating in the blood. The precise function of the eosinophils is not established, but they appear to be a first line of defense against parasitic invasions of the blood stream. They could also play a marked role in allergies and inflammation. Normally, a droplet of blood (e.g. a cubic millimeter) contains as many as 350 eosinophils. In patients with the ailment, EMS, there are 1,000-12,000 eosinophils per cubic millimeter.

In the fall of 1989, medical investigators at the Federal Center for Disease Control reported discovery of the reason for a recent outbreak of the rare disease, EMS, apparently, it was linked to at least one source of the nutritional supplement, L-tryptophan, which had become contaminated in the manufacturing process. L-tryptophan (L-TTP) (chemically, 1-alpha-aminoindole-3-propionic acid) is an essential amino acid, which is normally ingested as a constituent of dietary protein, but is not synthesized by the human body. It was first isolated from the milk protein, casein, early in this century. For many decades, L-tryptophan has been capable of laboratory synthesis by any of several routes, now well known in organic chemistry. Possibly, the once patented synthesis, starting with alpha-ketoglutaric acid phenylhydrazine, is the currently preferred mode of industrial-scale manufacture. Having a single asymmetric carbon atom, (alpha on the side chain), it is normally a mixture of two optically active antipodes.

L-tryptophan may be depicted by the planar structural formulas as follows:

HOOC—($NH_2$) CH—$CH_2$— Indole, with unsubstituted indole have the molecular formula $C_8H_7N$, also called 2,3-Benzopyrole.

L-tryptophan has long been approved by the Federal F & DA as a dietary supplement, but the compound has not yet been the subject of an approved New Drug Application (NDA), despite its established and expanding pharmacology in the literature. L-tryptophan is an essential nutrient with an estimated adult intake of 600 to 1220 mg daily.

In the formulation of L-tryptophan into dietary compositions, which are suitable for unit dosage administration, other [than] biologically inert compounds, like fillers and lubricants, are routinely employed; but heretofore, none of them have been recognized as being implicated in the newly observed EMS pathology in patients with some formulations of L-TTP.

EMS appears to have a subacute onset with clinical symptoms developing over several weeks. Patients typically complain of myalgia and fatigue. The myalgia is intense and often incapacitating. Many patients have respiratory complaints--dyspnea and cough, are especially common. There may be frank muscle weakness, distinct from any loss of extremity function caused by the severe myalgia. In some, the symptoms of EMS are distressing and serious and invite aggressive medical management.

As of Jan. 9, 1990, the number of officially reported EMS cases had climbed to 1046, for which the CDC has collected 429 completed report forms. In the evaluation of these forms, 98% had a history of L-tryptophan ingestion preceding the onset of symptoms. The duration of L-tryptophan use spanned from days to years with doses ranging from 26 mg to 15,000 mg per day; median, 1500 mg per day. 87% of the patients reported the onset of symptoms during or after July 1989, while 32% required hospitalization. Of the initial 30 cases reported (Nov. 13, 1989), eosinophil counts ranged from 2064 to 12,100 cells per mm; mean, 2300 cells per mm (normal; 50-350 cells per mm). [Presented are twenty cases satisfying the criteria for EMS as detailed by the CDC.]

CDC Criterion for Diagnosis of EMS (1) Eosinophil count of 1000 cells/mm or greater,
(2) Myalgias of severity sufficient to interfere with a patient's ability to pursue his or her usual activities
(3) exclusion of other infectious or neoplastic illness(es) that might account for 1 and 2.

Twenty patients were treated with steroid therapy (Dexamethasone, 0.5-4.0 mg/d; Carafate, 1 gr qid) for up to 3-4 months. Doses were administered in decreasing and tapered amounts relative to the degree of eosinophilia. All twenty patients were, for the most part, refractory to therapy and any slight improvement observed was lost within a few weeks following the cessation of steroids. In most cases steroid therapy had to be resumed.

OBJECTS OF THE INVENTION

It is a principal object of this invention to provide a formulation of the dietary supplement, L-tryptophan, which is free of ingredients that can lead to the blood abnormality, Eosinophilia in humans.

It is another object of the invention to provide a pharmaceutically acceptable formulation of LTP which can effectively treat the clinical symptoms and etiology of the condition now described as EMS.

It is still another object to provide a medical regimen which can return blood levels of the eosinophils to the normal range, where their elevation was caused by externally administered formulations of L-tryptophan.

A yet further object of the invention is to employ formulated L-tryptophan, in dosage unit form, for treatment of patient delirium after surgical trauma, as may be induced by a coronary bypass surgery.

SUMMARY OF THE INVENTION

Accordingly, the present invention permits the use of L-tryptophan as a dietary supplement but without the untoward clinical effects caused by certain of its formulations of this important amino acid. Concurrently, when Eosinophilia, and its attendant EMS, manifests itself clinically, the present discovery provides an alternative pharmaceutically-acceptable formulation of L-tryptophan that will obviate the toxic side effects perceived with certain of earlier formulations for this amino acid.

While the amino acid described herein has found widespread acceptance as a dietary supplment, its known pharmacology has led to its evaluation clinically in the treatment of certain common human ailments (see J. C. Caston, M. D., Clinical Applications of L-Tryptophan in the Treatment of Obesity and Depression, Advances in Therapy, Vol. 4, No. 2, March/April 1987).

The present invention relates to improved pharmaceutical preparations having positive pharmacologic effects on W.B.C. abnormalities, and to a method of treating EMS in mammals. The pharmaceutical composition of this invention are distinctive in that they will provide a dietary supplement, free of side-effects, and, more importantly provide a formulation with the pharmacologic advantage of treating the clinical symptoms of the newly recognized disease, EMS. Usually, they are given in conjunction with drug adjuncts, that all serve to purge the residual deleterious elements from the patient's system.

DETAILED DESCRIPTION OF THE INVENTION

Treatment Protocol and Clinical Observations

In light of the apparent ineffectiveness of steroid therapy, as well as the lack of treatment options, a treatment rationale was developed based upon the chemical analysis of the tryptophan-containing products. All twenty subjects had ingested the same brand of L-Tryptophan (1000 mg/tablets) which will be referred to as Brand "X". Samples of Brand "X" were obtained from these patients and analyzed against a control, pharmaceutical grade L-tryptophan [Trypto-Som (Tyson)]. Multiple samples of the control, both in powder and encapsulated forms, were provided by Tyson and Associates, Inc. (Santa Monica, Calif.) in sealed bottles of varying lot numbers. Analysis revealed that Brand "X" contained a significantly greater mineral content compared to control, especially calcium, magnesium and zinc (Table 1). The analysis of one Brand "X" tablet purchased in October, 1989 which was used by a patient with severe EMS exhibited vast differences in chemical composition compared to a sample of Brand "X" purchased before the summer of 1989 by another patient who did not develop EMS (see Table 2). In addition, a sample of Brand "X" raw material from earlier in 1989 was found to have somewhat similar mineral content as the Brand "X" tablet purchased before the summer of 1989. The uncompounded Brand "X" raw material has not been implicated in any EMS cases.

The Certificate of Analysis of the raw material specified the contents of the L-tryptophan, which had been granulated by methylcellulose, to contain a maximum heavy metal content of Lead (Pb)=0.0015% and arsenic $(AS_2O_3)=1.5$ ppm maximum. The zinc, magnesium, and calcium metal (mineral) contents were not listed. Analysis of the control pharmaceutical grade powder, [Trypto-Som (Tyson)] revealed less than 1 ppm for zinc, magnesium, calcium, lead, mercury, arsenic and cadmium. Differences between raw material composition points to a manufacturing difference in the two different raw materials even before encapsulation or tablet production.

Laboratory analysis of the implicated Brand "X" L-tryptophan tablets purchased by patients from June through October revealed increasing calcium and zinc levels throughout this time period, with the largest zinc ratios occurring in the fall of 1989 (Table II). A third tryptophan containing product was also analyzed. This product had been ingested by two nonaffected patients who had purchased the product earlier in 1989 and had mineral levels closer to the capsule control [Trypto-Som (Tyson)] capsules (Table II). Dramatic changes in mineral content continued to appear chronologically in July and August 1989 with the peak occurring in October 1989. Concomitant with the chronological changes occurring in the mineral contents was the presence of increasing residue after the tablets were ashed at 750° C.

Based upon the product analyses presented, one could attempt to develop a treatment regimen based upon a putative contaminant theory or a multiple contaminant theory. The latter might include an alteration of the L-tryptophan molecule itself during the manufacturing process. According to this theory, contaminant(s) are absorbed into the body whereby they then produce the clinical manifestations of EMS, presumably through an allergic type of reaction. Therefore, a therapeutic regimen was developed to reduce theorized excesses in zinc and calcium stearate and of the altered tryptophan molecules, if existent. Antagonism of these theorized allergens would presumably reduce the allergenic phenomenon expressing itself as EMS. The results of my study favor the contaminant theory since proper use of L-tryptophan plus ferrous sulfate, coordinated with zinc levels and complete blood counts contributed to the alleviation of EMS, rather than causing it.

Plasma magnesium and calcium levels from the twenty EMS patients were within normal ranges, while plasma zinc levels were found to be either elevated, or in the high normal (reference range 0.6 to 1.10 mg/ml) in all twenty patients with levels as high as 2.4 mg/ml. Consequently, a treatment strategy was developed to reduce zinc levels. The approach included supplemental ferrous sulfate to increase competition with zinc. Bicitra was used to increase urinary excretion through alkalization and to decrease itching. Trypto-Som (Tyson) was used to bind with zinc (via picolinic acid), as well as to displace the possibly altered L-Tryptophan molecules from the albumin molecule. Trypto-Som (Tyson) was also used to balance the ratio of L-tryptophan to Tyrosine and Phenylalanine since EMS patients with severe pain had decreased or reversed tryptophan/tyrosine ratio which normally 1.5:1 or 2:1.

Although each case required a customized treatment regimen, all of the twenty EMS patients received the following: 1) Iberet Folic 500 (1–2 Tablets/d); 2) Berroca (1 tab/d); 3) Bicitra (10–60 ml/d); 4) Trypto-Som (500–3000 mg/day); 5) Amino Opti-C (1000 mg/d); and 6) Carafate antiulcer therapy (1 gr/qid).

The above protocol was implemented in twenty EMS patients, initially refractory to steroid therapy. All patients were resumed on their previous steroid dosages. Some patients were switched to ferrous sulfate or ferrous gluconate elixir, in lower doses, if they developed an intolerance for Iberet Folic 500. The twenty cases included varying degrees of severity of clinical manifestations including fasciitis, polyneuropathies (to include partial stroke phenomena), optic neuritis with visual loss, and paraplegia. Several cases were also characterized by seizure disorders, metabolic encephalopathies, and myopathies.

After four to six weeks of treatment, Dexamethasone anti-inflammatory, Carafate and Amino Opti-C were gradually reduced and discontinued in all patients with cessation of eosinophilia and alleviation of EMS symptoms. Iberet Folic 500 was changed to every other day, or every third day) when hemoglobin levels were elevated to 13.5 or 14.0 and sluggishness developed. Berroca, Bicitra and Trypto-Som were continued, while Trypto-Som was gradually phased out when eosinophilia was lowered to less than 8%. Patients with pre-existing depression, anxiety disorders and other affective disorders, were gradually switched to a magnesium stearate free psychotropic medication (eg, Librium tranquilizer 25 mg, Prozac antidepressant 20 mg, Lithium carbonate capsule [Roxane], and Benadryl antihistamine 50 mg) while tapering off Trypto-Som.

No relapse occurred in any of the twenty patients in the 4-8 week period following the removal of steroid therapy. Zinc levels were monitored by serial analysis in all patients and lowered to low normal or below normal (0.60 mg/ml) as a result of the treatment regimen previously described. This directly correlated with the decrease and eventual alleviation of eosinophilia (counts less than 4%) and the associated EM symptoms. Plasma cortisol levels, zinc levels, complete blood counts, tryptophan levels, tyrosine levels and phenylalanine levels were monitored frequently. Plasma zinc and amino acid levels were performed by Medtox Laboratories of Minnesota.

Therapeutically and theoretically, the pathophysiology of EMS appears to be a toxic-allergic phenomenon that may not subside until the levels of non-physiologic zinc compounds, stearate compounds, and possibly other substances of known and unknown origin are reduced. An interplay between an altered tryptophan molecule and its interaction with zinc in the plasma must be also considered. Tyrosine may also play a role since the tyrosine/tryptophan ratio is reduced. Whether or not it plays a role in zinc metabolism is not determined, although its competition with tryptophan across the blood brain barrier is well-established. A theory proposed here is that tyrosine interacts with zinc compounds. So unless pure L-tryptophan is given to balance the tryptophan:tyrosine ratio in EMS patients, implementation of a chronic steroid regimen will drive the contaminants deeper into the tissues.

The problem with chronic ingestion of a potentially toxic allergen is that a critical mass is apparently a necessary requirement and thus one would expect varying degrees of EMS. Evaluation of 50 cases of EMS at many different stages supports this conclusion. Complete blood screening of 500 patients, taking many different brands and dosages of L-tryptophan, revealed no disease in 450 patients. In support of the theory of a chronic accumulation of tissue-bound and stored toxic allergens, one must take into consideration the course of events leading to recovery.

Detoxification of EMS patients must occur very slowly and follows a specific pattern of blood value events in the course of recovery from eosinophilia. The termination of this detoxification process appears to occur when a challenge of 900 mg ferrous sulfate does not cause a marked elevation in the baseline zinc levels, and no increase in the eosinophil count above 5% within 48 hours after the challenge. The challenge must be given to a patient who has been off of steroids for at least two weeks and has a baseline eosinophil count of less than 400 cells per mm.

All of the twenty cases who have been previously discussed have met these criterion. Although it would be too voluminous to discuss all of them, individually, five representative case-studies are presented.

Case #1

A 30 year old female who presented with seizures, eosinophilia, partial paraplegia and ataxia with an ascending polyneuropathy. Patient had neuropathies of the lower extremities and a grossly abnormal EMG. The patient presented as an outpatient 2 weeks before hospitalization with a 43% eosinophilia and a WBC count of 13,200. Dexamethasone (2 mg/g/d) was given, which decreased eosinophil count to 11-15% by the time of hospitalization. The patient also had a plasma zinc level of 2.43 mg/ml. Plasmapheresis was performed for one week. Within 48 hours after initiating plasmapheresis, the patient had a marked improvement in EMS symptoms. Nine days after the initiation of plasmapheresis, the patient was discharged to outpatient care and was walking with no assistance. The patient continued on Dexamethasone (0.5 mg/tid), but her eosinophilia did not decrease below 10% and symptoms were static for 10 days post hospitalization.

The patient was begun on Trypto-Som TM (2000-3000 mg/d) along with treatment plan outlined earlier. EMS was normal 4 weeks after discharge. At that time, the patient had an eosinophil and WBC count of 4% (400 cells/mm) and 9,100, respectively. Her plasma zinc level was 0.43 mcg/ml. Within 6 weeks after starting trypto-Som, Dexamethasone was discontinued without eosinophil remaining below 10%. Trypto-Som began to be tapered off 8 weeks post discharge and stabilized on Prozac antidepressant (20 mg/d), Librium tranquilizer (25 mg qid), Dilantin anti-epileptic (400 mg/d), and Nalfon anti-inflammatory (200 mg bid). Prior to developing EMS, the patient was on Mellaril tranquilizer (100 mg/d), Surmontil antidepressant (300 mg/d) and tryptophan (3000 mg/d) for the treatment of affective disorders.

Case #2

A 50 year old female presented with an eosinophil count of 60% and a WBC count of 15,400. The patient had ataxia, myalgia and polyneuropathy of the lower extremities with numbness bilaterally. Tissue biopsy of the quadriceps of the right leg showed vasculitis and inflammation infiltration by lymphocytes, eosinophilia, and a few plasma cells involving the ectodermal and mesodermal structures including nerves. The patient was treated with Dexamethasone (0.5 mg qid) along with the treatment described above. Trypto-Som (3000 mg/d) was given in divided dosages. Severe muscular pain of the lower extremities ceased within a few days after starting Trypto-Som. Upon admission, the patient was unable to walk without assistance and within 10 days of hospitalization, she was able to walk unassisted. Upon discharge, eosinophil and WBC counts were 25% and 7,900, respectively. Dexamethasone was discontinued eight weeks after discharge and after gradual tapering.

Trypto-Som was discontinued 10 weeks after discharge without any increase in eosinophil count over 4% or WBC counts over 7,000. The patient was on Tegretol anticonvulsant [carbamazepine] (500 mg/d), Prozac antidepressant (20 mg/q am), Librium tranquilizer (100 mg/d) and Berrocca multivitamin (1 tablet/d) with no reoccurrence of myalgia, itching or polyneuropathy symptoms. The patient is now driving and doing light housework. The patient was on disability for an atypical bipolar disorder that pre-existed EMS. Prior to developing EMS, the patient was on Methyl Dopa antihypertensive (123 mg/d), L-Tryptophan (3000 mg/d) and Klonopin anticonvulsant (18 mg/d). Plasma zinc level was 0.86 mcg/ml, several weeks after Trypto-Som therapy was begun. Eosinophilia stabilized below 4%, when plasma zinc levels plateaued at 0.5 mcg/ml.

Case #3

A 50 year old male developed severe itching, fasciitis in September 1989, and had eosinophilia of 18% and WBC count of 10,200. He was treated with Dexamethasone (0.5 mg bid) for 3 months, with inability to taper off of Dexamethasone without an increase in symptoms. Caffeine, red wine and shellfish would set off extreme itching and edema of the lower and upper extremities. In late December 1989, the patient was placed on Trypto-Som (1500 mg/d) as well as the treatment described above. Six weeks later, Dexamethasone was tapered off and then discontinued. Prior to Trypto-Som treatment plasma zinc level was 0.5 mcg/ml, but rose to 1.08 mcg/ml when ferrous sulfate and Trypto-Som were added to treatment regimen.

Eosinophilia did not reoccur and fasciitis decreased rapidly. Trypto-Som was then tapered and discontinued 8 weeks after treatment with trypto-Som had begun. The patient is currently on Haldo antidyskinetic (0.5 mg/d) and blood pressure medication. Prior to developing EMS, the patient had been taking L-Tryptophan (3000 mg bid), Klonopin anticonvulsant (1 mg qid), Aldomet antihypertensive and Maxzide diuretic. The patient had a twenty year history of a bipolar disorder with predominate depression symptoms. Fasciitis symptoms and areas of brown discoloration on all extremities are resolving gradually. No edema or erythema is present. Eosinophilia disappeared when plasma zinc levels were reduced gradually to 0.5 mcg/ml, although they initially rose with the addition of ferrous sulfate.

Case #4

A 40 year old male presented with pneumonitis symptoms and was hospitalized in December 1989. Eosinophil and WBC counts of 50% and 22,100 were found, respectively, upon admission. He had been hospitalized previously for 2 weeks in November for pneumonia. In September 1989, the patient had been put on L-Tryptophan (3500 mg/d) and Xanax antianxiety (2 mg/d) for the treatment of depression and anxiety. The patient also had a history of smoking 4 to 5 packs of cigarettes per day. The patient was started on Dexamethasone (0.5 mg qid) and L-tryptophan was discontinued. After 4 weeks of steroid treatment, no improvement in severe myalgia, joint pain, hair loss and fasciitis symptoms was seen.

The patient was started on Trypto-Som (500 mg qid) along with the treatment described above. The patient reported that when pneumonitis symptoms worsened in December 1989 that he noticed a metallic taste when he would cough up sputum. After 4 weeks of Trypto-Som and Iberet Folic treatment, Dexamethasone was discontinued after tapering, Trypto-Som was discontinued and the patient was switched to Prozac antidepressant (20 mg q am). No eosinophilia over 4% has reoccurred while WBC counts remain less than 11,000. Pneumonitis, myalgia and fasciitis symptoms have disappeared since Dexamethasone and Trypto-Som discontinuation while plasma zinc levels were 0.5 mcg/ml or less.

Case #5

A 67 year old male was admitted to the hospital with confusion, seizures and severe fasciitis of the lower extremities, and a WBC count of 13,700 and an eosinophil count of 33%/ After admission to a psychiatric unit the patient developed T-Wave inversions in the anterior precordium and was transferred to a coronary care unit. Several cardiac enzymes were negative for myocardial infarct. His chest x-ray showed congestive heart failure with minimal infiltrate at the left base. After treatment with intravenous fluids, cardiac monitoring, Dexamethasone 4 to 6 mg per day, broad spectrum antibiotics (Depakote anticonvulsant and Phenobarbital), the patient stabilized and was diagnosed as having acute bronchitis, eosinophilia myalgia syndrome, chronic obstructive pulmonary disease, myocardial ischemia (suspected but not found) and congestive heart failure. After medical stabilization, the patient was transferred back to a psychiatric unit for regulation of medication for treatment of a bipolar disorder.

The patient had been taking Brand "X" L-tryptophan (3000–4000 mg/d) prior to admission along with Lithium carbonate (600 mg/d) and Phenobarbitol (60 mg). The patient also was drinking 6 ounces of alcohol per day. After stabilization the patient was discharged on Dexamethasone (0.5 mg/d) with a WBC and eosinophil count of 8,500 and 4%, respectively. Two weeks post hospitalization, the patient began to regress with increased joint pain and fasciitis symptoms. Plasma zinc level was 1.02 mcg/ml and an plasma tryptophan level of 29 micromoles/L (69–146 normal) with eosinophilia increasing to 10% with a WBC count of 9,100. The patient was begun on Trypto-Som (500 mg q hs) for one month. When plasma zinc level reached 0.59 mcg/ml and eosinophil count reached 4%, Dexamethasone and Trypto-Som was discontinued. Six weeks after discontinuation of Dexamethasone and Trypto-Som, WBC count was 9,300 and eosinophils 2%. No EMS symptoms were present. The patient is now taking Eskalith LiCO$_3$ (450 mg/d), L$_1$ (O$_3$) Depakote (250 mg tid), phenobarbital (30 mg hs), Lasix (40 mg q AM), diuretic, Potassium (10 mEq/d), and Synthroid synthetic L-thyroxine (0.1 mg/d).

CLINICAL USE IN TREATING POST-CARDIOPULMONARY BYPASS DELIRIUM PATIENTS

Case #6

The patient is a 62-year-old white male who was hospitalized for emergency treatment of acute chest pain. He was admitted on Day 1 by his cardiologist who performed cardiac catheterization which revealed occlusion in two coronary arteries. After an his thoracic surgeon on Day 1 of admission, the patient had an uncomplicated post-surgical period in the cardiovascular recovery unit on Days 1, 2, and 3. On Day 4 the patient developed acute symptoms of confusion, memory dysfunction, and agitation. He was amnestic for post-op Days 1 to 6.

An emergency amino acid panel revealed the following: L-tryptophan=72 umol/L (normal 69–147); tyrosine=67 umol/L (normal 33–88); phenylalanine=52 umol/L (normal 55–110). A DST on Day 5 revealed cortisol levels of 5.0 ug/dL at 7:00 AM and 3.0 ug/dL at 4:00 PM (FIG. I). Repeat DSTs revealed cortisol levels of 3.0 ug/dL at 7:00 AM and 3.4 ug/dL at 4:00

PM on Day 8 and 2.0 ug/dL at 7:00 AM and 4:00 PM on Day 11 (FIG. II). The patient was treated with L-tryptophan 2000 mg over a four- to five-hour period on Day 4 when he was seen by a psychiatric consultant.

The patient's delirium, insomnia, confusion, and recent time disorientation cleared up by Day 9 on L-tryptophan 1000 mg at 4:00 PM and 1500 mg at bedtime. By Day 8, cortisol levels at 7:00 AM and 4:00 PM were <3.5 ug/dL and were converting into a normal suppressed state. One Day 9 the patient's mental status had completely normalized and by Day 11 the DST had also normalized. Thus, normalization of the DST occurred 48 hours after the normalization of the patient's mental status. Amino acid panel results are summarized in Table 3. The application and use of the dexamethasone suppression test (DST) as a state-related neuroendocrine marker in post-cardiopulmonary bypass delirium has not been utilized in other reported studies.

Patient #6 received no phenothiazines, anxiolytics, or hypnotics. He was managed only with L-tryptophan 1500 mg at bedtime after the date of discharge on Day 12 of hospitalization. A repeat DST 35 days later revealed cortisol levels <2.0 umol/L. He had no delirium residual and discontinued L-tryptophan six weeks after hospitalization with no complications.

Overview

The rapid increase in EMS cases beginning July 1989 suggests contamination rather than something inherent in tryptophan itself. It is known that L-Tryptophan can be converted metabolically by rumen microflora to 3-methylindole which is thought to be a toxin in bovine atypical interstitial pneumonia. The authors note however that their patients did not fit the clinical or pathological features of adult respiratory distress syndrome.

Patient #4 tolerated the addition of L-tryptophan (Trypto-Som) back to his treatment regimen and pneumonitis symptoms improved relative to cessation of eosinophilia. The zinc and calcium stearate found in Brand "X" tryptophan might be feasible as an explanation for the allergic induced pulmonary disease as a tryptophan metabolite. Tissue biopsy of patient #2 showed infiltration of lymphocytes, plasma cells, and eosinophil in nerve and muscle tissue as well as vasculities in a lower extremity biopsy.

Compound Syntheses and Pharmaceutical Formulations

There are several U.S. Patents describing biological methods of its production. For example, L-Tryptophan is produced by a fermentation process comprising culturing hydro-carbonassimilating microorganism under aerobic conditions in an aqueous nutrient medium, containing one or a mixture of such hydrocarbons as carbon source and precursor amounts of anthranilic acid. Typical organisms include breribacterium ketoglutaricum, U.S. Pat. No. 3,591,456, issued Jul. 7, 1971 to Keiichi I, et al.

The purified L-tryptophan employed in this invention may be generated biochemically by the hydrolysis of proteins (yielding both optical isomers); or more practically, by one of the known synthesis methods. Typical of these synthesis are Indole to gramine (N,N-Dimethyl-1H-Indole-3-Methanamine), followed by methylation, interaction with acetylaminomalonic ester and hydrolysis. Leaflets or plates are recovered from dilute alcohol, dec. at 289° F.

The amino acid is soluble in water, hot alcohol, in alkali hydroxides and insoluble in chloroform. The hydrochloride salt, $C_{11}H_{12}N_2O_2.HCl$, forms needles from methanol, dec. 251° F. It is available commercially in all three forms, as well as acetyl-D L-tryptophan.

U.S. Pat. No. 4,497,957, issued Feb. 5, 1985 is to a process for preparing optically active tryptophans. Biochemical optical resolution of the racemic (DL) mixture starts with a microorganism capable of producing the enzyme amidase. The L-Tryptophan amide compound in racemic DL tryptophan are asymmetrically hydrolyzed to form optically active L-isomer at high yield without the D-isomer being subject to hydrolysis. After isolating the L-isomer, the D-isomers can be readily hydrolyzed to the acid.

Most advantageously, the compositions of this invention, in dosage unit form, comprise a nontoxic pharmaceutical carrier and the above-described active compound, or one of its pharmaceutically-acceptable acid addition salts.

It will be readily apparent to one skilled in this art that the substituted aliphatic amine compounds of this invention has one asymmetric carbon atom, forming optically active d- and l-compounds. The connotation of the molecular formula presented herein is intended to include the separated d- or l-optical isomers, as well as racemic mixtures of these isomers (d=dextro-rotatory).

If desired, the isomers may be separated for individual use by resolution methods known to the art, such as fractional crystallization. Alternatively, a synthesis starting with an optically active component may lead to the desired optical isomer.

A nontoxic pharmaceutically acceptable organic or inorganic acid addition salt of the base acid may be used instead of the base compound; preferably, the hydrochloride salt is used. However, other salts such as those derived from sulfuric, nitric, phosphoric, citric, acetic, lactic, mandelic, salicylic, phthalic, fumaric, maleic, tartaric, hydrobromic, benzoic, and like nontoxic acids, may be used. The salts are best prepared by reacting the free base with a stoichiometric amount of the desired organic or inorganic acid in a suitable solvent, such as ethyl acetate-ether solution, ethanol, acetone, water or various combinations of solvents. In addition to the acid addition salts, the quaternary ammonium salts may be employed.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly the carrier or diluent include any time delay material well known to the art, such as glycerol monostearate or glycerol distearate, alone or with a wax.

A wide variety of pharmaceutical forms can be employed. Thus, if a solid carrier is used the preparation can be tableted, placed in a hard gelatin capsule in powder or pellet form or in the form of a troche or lozenge. The amount of solid carrier will vary widely, but preferably will be from about 25 mg to about 1 g. If a liquid carrier is used, the preparation will be in the form of a syrup, emulsion, soft gelatin capsule, ampul or liquid suspension.

The method of treatment in accordance with this invention comprises administering orally to an afflicted patient, the amino acid known as L-tryptophan, or a non-toxic addition salt thereof, usually combined with a pharmaceutical carrier, i.e., any of the above compositions in a dosage sufficient to product symptomatic relief over an extended period of 30 to 180 days. There is usually concurrent administration of other drugs for palliative purposes as described in the clinical cases.

These active medicaments preferably will be, typically per unit of free base, in an amount from about 400 to 600 mg., and advantageously from about 450 g. to about 550 mg. Advantageously equal doses will be administered one to six times daily. Preferably, the daily dosage regimen will be from 1000 mg. to 3000 mg. of active medicament in pharmaceutical form. At the higher daily dosage, two or more capsules may be taken at each administration to attain the intended dosage level.

The following example is not limiting but should be construed as illustrative of useful pharmaceutical preparations of this invention.

EXAMPLE 1

| Ingredients: | Amount (mgs.) |
|---|---|
| L-tryptophan | 500 |
| Ascorbyl Palmitate | 25 to 50 |

The above ingredients will be of a grade that satisfies United States Pharmacopia (USP) standards, classifying the ingredients as pharmaceutical grade. They will be mixed together and filled into #1 hard gelatin capsule. One such capsule contains 500 mg. of active ingredient, and are administered several times daily, dependent upon the dosage regiment determined as suitable for the specific patient. One commercial source of L-tryptophan is produce chemically by Tanabe, U.S.A., Inc.

TABLE I

Analysis of L-Tryptophan products (numerical values represent metals in parts per million (PPM).

|  | Control [Tryptosom (Tyson)] | | Brand "Y" Tryptophan 1000 mg | Brand "X" Tryptophan used by one severe EMS |
|---|---|---|---|---|
|  | Powder | Capsule | Fall 1989 | Patient |
| Zinc | 0.6 | 2 | 1 | 135 |
| Magnesium | 0.5 | 560* | 1,011 | 1,240 |
| Calcium | 0.4 | 10 | 47 | 29,013 |
| Mercury |  |  | less than 1.0 |  |
| Mercury |  |  | less than 1.0 |  |
| Ash Analysis | no residue | small amt |  | large amt very fine blk residue |

|  | Brand "X" Tryptophan Tablet | Brand "X" Tryptophan Tablet Early 1989 (no EMS) | Showa Denko Trypotohan raw Material (early 1989) No EMS linked at time |
|---|---|---|---|
| Zinc | 1 | 2 | 2.3 |
| Magnesium | 703 | 489 | 707 |
| Calcium | 54 | 38 | 45 |
| Lead |  | less than 1.0 |  |
| Mercury |  | less than 1.0 |  |
| Ash Analysis | small amount white residue | small amount grey residue | no residue |

*from magnesium stearates necessary for encapsulation.

TABLE II

Chronological Analysis of Brand "X" L-tryptophan 1000 mg Tablets (Numerical values represent metals in parts per MILLION)

|  | Brand "X" 1988 | Brand "X" April 1989 | Brand "X" May 1989 | Brand "X" June 1989 | Brand "X" July 1989 |
|---|---|---|---|---|---|
| Zinc | 1 | 2 | 17 | 1 | 18 |
| Magnesium | 703 | 489 | 659 | 599 | 787 |
| Calcium | 54 | 38 | 422 | 53 | 3,388 |
| Lead | 1 | 1 | 1 | 1 | 1 |
| Mercury | 1 | 1 | 1 | 1 | 1 |
| Ash Analysis | no residue | no residue | small am't grey residue | small am't white residue | medium am't blk residue |
| Patient Symptoms | No EMS | No EMS | No EMS | EMS Fasciitis | EMS Fasciitis |

|  | Brand "X" Aug. 1989 | Brand "X" Sept. 1989 | Brand "X" Oct. 1989 | Brand "X" Nov. 1989 |
|---|---|---|---|---|
| Zinc | 3 | 84 | 199 | 135 |
| Magnesium | 837 | 1,143 | 1,354 | 1,240 |
| Calcium | 12,908 | 11,667 | 478,041 | 29,013 |
| Lead | 1 | 1 | 1 | 1 |
| Mercury | 1 | 1 | 1 | 1 |
| Ash Analysis | medium am't of black residue | large am't of fine blk residue | large am't of fine blk residue | large am't of fine blk residue |

TABLE II-continued

Chronological Analysis of Brand "X" L-tryptophan 1000 mg Tablets
(Numerical values represent metals in parts per MILLION)

| Patient Symptoms | EMS Fasciitis | EMS Polyneuropathy | EMS Fasciitis | EMS, Polyneuropathy Paraplegia, Seizures |
|---|---|---|---|---|

TABLE III

Patient #6: Amino acid Panel

| | L-Tryptophan* (umol/L) | Tyrosine** (umol/L) | Phenylalanine*** (umol/L) |
|---|---|---|---|
| Day 4 (8:20 PM) | 72 | 67 | 54 |
| Day 6 (7:00 AM) | 113 | 65 | 80 |
| Day 7 (6:00 AM) | 116 | 101 | 93 |
| Day 9 (6:00 AM) | 160 | 66 | 63 |
| Day 35 (9:00 AM) | 86 | — | — |

*(normal 69–147)
**(normal 33–88)
***(normal 55–110)

I claim:

1. A pharmaceutical composition in unit dosage form, which consists essentially of:
   (a) one or more pharmaceutically acceptable formulations, comprising a minor amount of solid or liquid carrier selected from one or more of lactose, terra alba, sucrose, gelatin talc, gelatin, agar, pectin, acacia, magnesium stearate, stearic acid, ascorbyl palmitate, sugar syrup, peanut oil, olive oil, and water; and
   (b) a major amount of the amino acid, pharmaceutical grade L-Tryptophan, or a pharmaceutically acceptable organic or inorganic, acid addition salt thereof, which is effective to treat refractory Eosinophilia-Myalgia Syndrome in a patient to whom one or more unit dosages of the formulated amino acid is to be administered; and
   (c) as to said solid carriers said liquid carriers and said pharmaceutically acceptable salts, such adjuvants are selected to exclude the zinc, magnesium, and calcium containing salts.

2. In a method of using a pharmaceutical composition containing one or more pharmaceutically acceptable formulations of an active ingredient and a solid or liquid carrier therefore novel for treating a human being with refractory Eosinophilia-Myalgia Syndrome, the improvement characterized by compounding as an active ingredient, a major amount of the amino acid, pharmaceutical grade L-Tryptophan, or a pharmaceutically-acceptable, organic or inorganic, acid addition salt thereof and a minor amount of a solid or liquid carrier, selected from one or more of lactose, terra alba, sucrose, gelatin talc, gelatin, agar, pectin, acacia, magnesium stearate, stearic acid, ascorbyl palmitate, sugar syrup, peanut oil, olive oil, and water in a unit dosage form, effective to treat said syndrome, such adjuvants are selected to exclude the zinc, magnesium, and calcium containing salts, as determined by reducing over time the elevated serum count of eosinophil cells to the normal range substantially above 350 eosinophil cells per cubic millimeter of blood, further comprising orally administering a therapeutically effective amount to an afflicted patient a daily dosage regimen of about 1000 mg. to about 3000 mg. of the active ingredient until the serum count of such cells is measured as having returned to the normal range.

3. The method of reducing elevated levels of eosinophil cells in a human patient which comprises:
   (a) orally administering to a human patient needing suppression of said abnormal cell levels a daily dosage regimen from about 1000 mg. to about 3000 mg. of the amino acid, L-tryptophan, selected from one of its free base and its non-toxic, pharmaceutically acceptable acid addition salts.

4. The composition of claim 1 wherein the unit dosage form is a tablet containing from 400 to 600 milligrams of L-Tryptophan and from 25 to 50 milligrams of a solid carrier.

5. The method of claim 2 wherein the treatment effective amount is a daily dosage regimen from about 1000 gm to about 3000 gm of a free base and its non-toxic, pharmaceutically acceptable acid addition salts.

6. The method of claim 2 wherein the unit dosage form is a tablet containing from 400 to 500 milligrams of the L-tryptophan.

7. The method of claim 6 wherein the unit dosage form is administered one to six times daily.

8. The composition of claim 1 wherein the unit dosage form is a syrupy diluent volume containing 400 to 600 milligrams of the amino acid.

9. A method of treating a human patient diagnosed with refractory Eosinophilia-Myalgia Syndrome, as can be characterized by abnormally elevated serum levels of eosinophil cells, which is substantially above 350 cells per cubic millimeter of blood comprising orally administering a therapeutically effective amount to such a patient of a daily dosage regimen of from about 1000 mg. to about 3000 mg. of the pharmaceutical composition of claim 1 over a period of 30 to 80 days sufficient to produce clinically observable symptomatic relief, for those in need thereof.

10. The composition of claim 1 wherein the minor amount of solid carrier comprises ascorbyl palmitate encapsulated with said amino acid in a gelatin capsule.

* * * * *